US 6,556,008 B2

(12) United States Patent
Thesen

(10) Patent No.: US 6,556,008 B2
(45) Date of Patent: Apr. 29, 2003

(54) METHOD FOR OPERATING A MAGNETIC RESONANCE IMAGING APPARATUS ENSURING COINCIDENCE OF IMAGES OBTAINED IN DIFFERENT EXAMINATIONS WITH RESPECTIVELY DIFFERENT POSITIONS OF A SUBJECT

(75) Inventor: Stefan Thesen, Meckenheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/881,589

(22) Filed: Jun. 14, 2001

(65) Prior Publication Data
US 2002/0005718 A1 Jan. 17, 2002

(30) Foreign Application Priority Data
Jun. 15, 2000 (DE) ......... 100 29 585

(51) Int. Cl.⁷ .................................. G01V 3/00
(52) U.S. Cl. ...................... 324/307; 324/309
(58) Field of Search ................. 324/307, 309

(56) References Cited

U.S. PATENT DOCUMENTS

| 4,871,966 A | * | 10/1989 | Smith et al. | 324/309 |
| 5,613,492 A | * | 3/1997 | Feinberg | 324/307 |
| 5,886,524 A | | 3/1999 | Krieg | 324/312 |
| 6,026,315 A | | 2/2000 | Lenz et al. | 600/414 |
| 6,157,194 A | * | 12/2000 | Vassallo et al. | 324/312 |
| 6,198,959 B1 | * | 3/2001 | Wang | 324/307 |
| 6,230,040 B1 | * | 5/2001 | Wang et al. | 324/309 |
| 6,268,730 B1 | * | 7/2001 | Du | 324/309 |
| 6,421,551 B1 | * | 7/2002 | Kuth et al. | 324/307 |

FOREIGN PATENT DOCUMENTS

EP        0 909 958        4/1999

OTHER PUBLICATIONS

"Human Brain Function," Frackowiak et al., Academic Press (1997) pp. 43–58.
"Movement–Related Effects in fMRI Time–Series," Friston et al., Magnetic Resonance in Medicine, vol. 35 (1996) pp. 346–355.
"Decoupled Automated Rotational and Translational Registration for Functional MRI Time Series Data: The DART Registration Algorithm," Maas et al., Magnetic Resonance in Medicine, vol. 37 (1997) pp. 131–139.
"Symmetric Phase–Only Matched Filtering of Fourier–Mellin Transforms for Image Registration and Recognition," Chen et al., IEEE Trans. on Pattern Analysis and Machine Intelligence, vol. 16, No. 12 (1994) pp. 1156–1168.

* cited by examiner

Primary Examiner—Edward Lefkowitz
Assistant Examiner—Dixomara Vargas
(74) Attorney, Agent, or Firm—Schiff Hardin & Waite

(57) ABSTRACT

In a method for the operation of a magnetic resonance apparatus, in a first examination of an examination subject, a first scout dataset of the examination subject is produced and with reference to which at least one first slice of an examination subject to be imaged is determined. A further scout dataset of the examination subject is produced in at least one further examination of the examination subject temporally following the first examination. A change in position between the first and the further scout dataset is identified, and at least one further slice of the examination subject to be imaged is defined according to the identified positional change, this at least one further slice exhibiting an identical positioning within the examination subject with respect to the first slice.

6 Claims, 1 Drawing Sheet

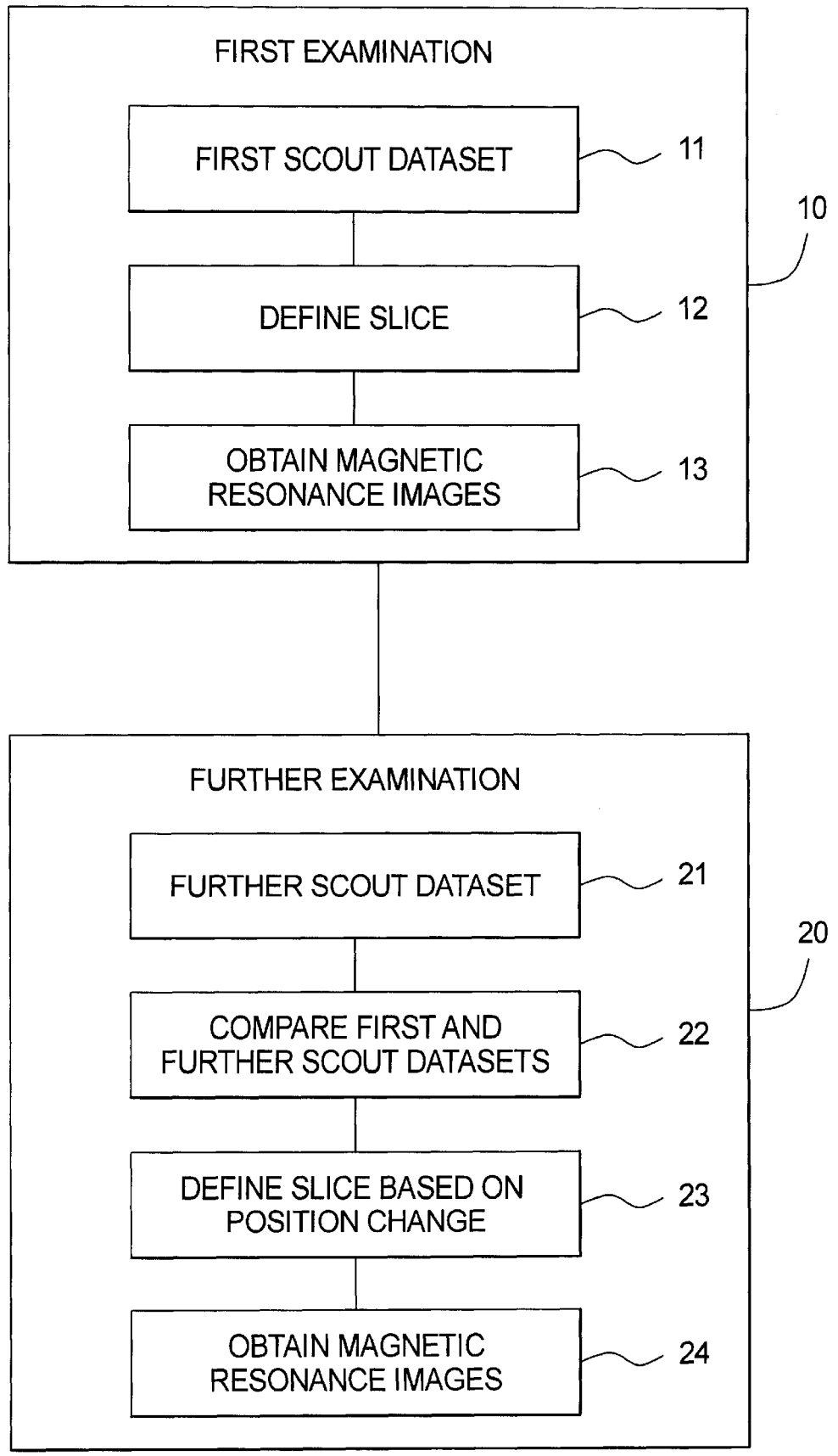

METHOD FOR OPERATING A MAGNETIC RESONANCE IMAGING APPARATUS ENSURING COINCIDENCE OF IMAGES OBTAINED IN DIFFERENT EXAMINATIONS WITH RESPECTIVELY DIFFERENT POSITIONS OF A SUBJECT

BACKGROUND OF THE INVENTION

1. Field of the Invention

The present invention is directed to a method for operating a magnetic resonance apparatus, particularly for the purpose of obtaining identically positioned slice images of a subject in temporally separated examinations.

2. Description of the Prior Art

Magnetic resonance technology is a known technique for acquiring images of the inside of the body of an examination subject. In magnetic resonance imaging, rapidly switched gradient fields that are generated by a gradient system are superimposed on a static, basic magnetic field in a magnetic resonance apparatus. The magnetic resonance apparatus also has a radio-frequency system that omits radio-frequency signals into the examination subject for triggering magnetic resonance signals, and that picks up the generated magnetic resonance signals. Image datasets and magnetic resonance images are produced on the basis of the image datasets.

In functional magnetic resonance imaging, a sense of image datasets is registered in a time sequence from the same area of an examination subject to be imaged. Appropriate methods are known for filtering out differences between the image datasets that are the result of a change in position of the region to be imaged with respect to the apparatus during the time sequence.

One group of methods for determining positional change from image data sets registered in chronological succession is based on a description of an arbitrary rigid body movement in three-dimensional space with six motion parameters, whereby three parameters identify translations and three parameters identify rotations. The parameters are represented, for example, in a column vector $\vec{q}$. The values of all voxels or selected voxels of a first image dataset and of a second, subsequently obtained image dataset, are respectively represented in a first column vector $\vec{x}$ and in a second column vector $\vec{y}$ in a coinciding sequence. The following equation, which is based on a Taylor expansion of the first order, is solved for determining a positional change between the registration times of the first and of the second dataset, i.e. for determining the motion factor, for example with an iterative method:

$$\vec{y} - \vec{x} = \begin{bmatrix} \frac{\partial x_1}{\partial q_1} & \cdots & \frac{\partial x_1}{\partial q_6} \\ \vdots & \ddots & \vdots \\ \frac{\partial x_n}{\partial q_1} & \cdots & \frac{\partial x_n}{\partial q_6} \end{bmatrix} \cdot \vec{q} \text{ with } \vec{x} = \begin{bmatrix} x_1 \\ \vdots \\ x_n \end{bmatrix}; \vec{y} = \begin{bmatrix} y_1 \\ \vdots \\ y_n \end{bmatrix}; \vec{q} = \begin{bmatrix} q_1 \\ \vdots \\ q_6 \end{bmatrix}$$

More detailed descriptions of acquisition algorithms for positional changes based on image datasets, are available in the book by R. S. J. Frackowiak et al, *Human Brain Function*, Academic Press, 1997, particularly chapter 3, pages 43 through 58, and the article by K. J. Friston et al. "Movement-Related Effects in fMRI Time-Series" Magnetic Resonance in Medicine 35 (1996), pages 346 through 355.

In another group of methods for acquisition of positional change based on image datasets, all points or specific, selected points of a first image dataset described in k-space, and of a second image dataset that has been produced following the first in terms of time, are compared to one another. The methods are based on the fact that, due to a change in position between the registration times of the two datasets, translations and/or rotations of the region to be imaged are represented by a modification of the phase and/or the magnitude of respective data points that are identically arranged within the two datasets. Embodiments of this type of method are described in greater detail in, for example, the article by L. C. Maas et al, "Decoupled Automated Rotational and Translational Registration for Functional MRI Time Series Data: The DART Registration Algorithm", Magnetic Resonance in Medicine 37 (1997) pages 131 through 139, as well as in the article by Q. Chen et al., "Symmetric Phase-Only Matched Filtering of Fourier-Mellin Transforms for Image Registration and Recognition", IEEE Transactions on Pattern Analysis and Machine Intelligence, volume 16, number 12 (1994), pages 1156 through 1168.

It is standard for maintaining sequence control calibration in patient treatment regimens which require multiple sessions, to repeatedly image the same region of an examination subject in successive examinations with a magnetic resonance apparatus that are spaced in time from one another. These examinations can ensue, for example, at a time spacing of a few hours or weeks. In an examination following a first examination, the operator of the magnetic resonance apparatus tries to position the examination subject in the apparatus and to set the apparatus with manual inputs so that the images to be registered correspond as closely as possible to those of the first examination with respect to positioning within the examination subject. Only a moderate coincidence can be achieved by such manual adjustment. Further, the degree of the coincidence is dependent on the respective operator. Moreover, such manual adjustment is comparatively time-consuming.

SUMMARY OF THE INVENTION

An object of the present invention is to provide a method for the operation of a magnetic resonance apparatus that, among other things, alleviates the aforementioned disadvantages associated with a sequence control calibration.

This object is inventively achieved in a method for the operation of a magnetic resonance apparatus wherein in a first examination of an examination subject, a first scout dataset of the examination subject is produced and with reference to which at least one first slice of the examination subject to be imaged is determined, and wherein a further scout dataset of the examination subject is produced in at least one further examination of the examination subject temporally following the first examination, and wherein a change in position between the first scout dataset and the further scout dataset is identified, and wherein at least one further slice of the examination subject to be imaged is defined according to the identified positional change, this at least one further slice exhibiting an identical positioning within the examination subject with respect to the first slice.

The inventive method allows the magnetic resonance apparatus to be set automatically, with high precision and in a time-efficient way in the further examination, so that the magnetic resonance images to be generated in the further examination exactly coincide with those of the first examination with respect to positioning within the examination subject. As a result, the ability to compare the magnetic resonance images is maximized. Differences between magnetic resonance images of the first examination and of the further examination are precluded, so that, for example, pathological changes can be clearly diagnosed as such.

In an embodiment, the above-described method for determining changes in position from image datasets on the basis of a first order Taylor expansion is utilized for the determination of the change in position.

In another embodiment, the scout datasets are generated as three-dimensional image datasets, particularly with a fast imaging technique, for example an echo planar method. As a result, arbitrary rotations and/or translations in the three-dimensional space can be determined from the scout datasets as changes in position. Further, the scout datasets can be registered in a time-efficient way.

In a further embodiment, the examination subject in the further examination is automatically positioned in the magnetic resonance apparatus in conformity with data stored for the first examination. In a first version, the examination subject in the further examination is thereby seated on a support mechanism in conformity with the first examination. This means that the patient is seated on his/her back and with the head in front in conformity with the first examination. Subsequently, a displacement of the support mechanism for positioning the region of the examination subject to be imaged in the imaging volume of the apparatus is automatically implemented on the basis of the stored data from the first examination and without an intervening pause, for example employing a laser sighting arrangement that marks the region to be imaged. In another version, the patient is arbitrarily seated on the support mechanism in the further examination within a predetermined position range. A camera system thereby acquires the contours of the patient dependent on the type of patient support. In conjunction with the stored data of the first examination, a displacement of the support mechanism is determined and implemented, so that the same region of the patient to be imaged is positioned in the imaging volume in the further examination as in the first examination.

DESCRIPTION OF THE DRAWINGS

As an exemplary embodiment of the invention, the FIGURE shows a flowchart for a sequence control on the basis of magnetic resonance images.

DESCRIPTION OF THE PREFERRED EMBODIMENTS

As shown in the FIGURE, the sequence control in accordance with the invention begins with a first examination 10 at a first point in time. After a positioning of a region, for example an abdominal region, of a patient to be examined in the imaging volume of a magnetic resonance apparatus, a first scout dataset of the region to be images is generated in the step 11. On the basis of this first scout dataset, a definition of diagnostically relevant slices by a diagnosing physician ensues in the step 12. Magnetic resonance images are registered in a step 13 according to the defined slices.

After a few days, the same region to be imaged in the same patient is reexamined for checking the outcome of a treatment. For this purpose, the same region for imaging is positioned in the imaging volume of the apparatus during the course of the further examination. A physical positioning that is completely identical with respect to the first examination is not possible because the patient cannot be positioned with millimeter precision on the support mechanism of the apparatus. After approximate positioning, a further scout dataset 21 is generated in the further examination 20. In a step 22, the further scout dataset is compared to the first scout dataset in a control system of the apparatus. To that end, the control system can employ one of the previously described methods. In a step 23, a definition of slices to be imaged ensues such on the basis of the change in position determined in the step 22 so that the slices of the further examination 20 correspond to the slices of the first examination 10 with respect to positioning within the patient. Finally, a corresponding magnetic resonance image generation of the slices defined in step 23 ensues in step 24. Differences between a magnetic resonance image of the first examination 10 and a magnetic resonance image of the second examination for the same slice 20 are direct indications of a positive or negative treatment outcome for the diagnosing physician. Differences as a consequence of non-congruent slices in the first examination 10 and the second examination 20 as well as misinterpretations arising therefrom are thus reliably precluded.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a magnetic resonance apparatus, comprising the steps of:

in a first examination of a subject in a first position in a magnetic resonance apparatus, obtaining a first scout dataset, representing magnetic resonance signals from said subject, and subsequently defining a first slice of said subject based on said first scout dataset;

repositioning said subject to a second position, different from said first position, in said magnetic resonance apparatus and, in a further, subsequent examination of said subject in said magnetic resonance apparatus, obtaining a further scout dataset, representing magnetic resonance signals from said subject;

identifying a change in said position of said subject between said first scout dataset and said further scout dataset; and defining a further slice of said examination subject dependent on said change in position, said further slice having an identical positioning within said subject as said first slice.

2. A method as claimed in claim 1 wherein the step of identifying said change in position comprises the steps of:

representing at least selected values of said first scout dataset in a first vector;

identifying values of said second scout dataset, respectively corresponding to said selected values of said first scout dataset, and representing said values of said second dataset in a second vector;

representing six parameters in a third vector, which allowed description of an arbitrary change in position in three-dimensional space;

forming a Jacobi functional matrix having a plurality of rows wherein each of said rows is comprised of partial derivatives of respective values of said first vector with respect to said six parameters, and forming a first order tailor expansion equation wherein a difference between said second vector and said first vector is set equal to a product of said Jacobi functional matrix and said third vector; and solving said equation by an iterative technique to determine said six parameters.

3. A method as claimed in claim 1 comprising generating said first scout dataset as a three-dimensional image dataset and generating said further scout dataset as a three-dimensional image dataset.

4. A method as claimed in claim 1 comprising generating said first scout dataset with a fast magnetic resonance imaging technique and generating said further scout dataset with a fast magnetic resonance imaging technique.

5. A method as claimed in claim 4 comprising generating said first scout dataset with an echo planar technique and generating said further scout dataset with an echo planar technique.

6. A method as claimed in claim 1 comprising automatically positioning said subject in a magnetic resonance apparatus in said further examination using data stored from said first examination.

\* \* \* \* \*